US010016531B2

(12) United States Patent
Vad et al.

(10) Patent No.: US 10,016,531 B2
(45) Date of Patent: *Jul. 10, 2018

(54) METHOD FOR ELECTROSPINNING A GRAFT LAYER

(71) Applicant: COOK MEDICAL TECHNOLOGIES LLC, Bloomington, IN (US)

(72) Inventors: Siddharth U. Vad, Bloomington, IN (US); Mark A. Magnuson, Bloomington, IN (US); Mark R. Frye, Bloomington, IN (US); Sean D. Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 300 days.

This patent is subject to a terminal disclaimer.

(21) Appl. No.: 14/852,199

(22) Filed: Sep. 11, 2015

(65) Prior Publication Data

US 2016/0000976 A1    Jan. 7, 2016

Related U.S. Application Data

(63) Continuation of application No. 13/548,956, filed on Jul. 13, 2012, now Pat. No. 9,163,333.
(Continued)

(51) Int. Cl.
*B32B 1/08* (2006.01)
*B32B 5/24* (2006.01)
(Continued)

(52) U.S. Cl.
CPC ........ *A61L 31/041* (2013.01); *B29C 47/0014* (2013.01); *B29C 47/0064* (2013.01); *B29C 47/06* (2013.01); *D01D 5/0038* (2013.01); *D01D 5/0069* (2013.01); *D01D 5/0084* (2013.01); *D04H 1/728* (2013.01); *D04H 3/073* (2013.01);
(Continued)

(58) Field of Classification Search
CPC .. B29C 47/06; B32B 1/08; B32B 5/24; B32B 2250/03; D01D 5/003; D01D 5/0038; D01D 5/0046; D01D 5/0084
USPC ........ 264/10, 171.1, 171.26, 171.27, 171.29, 264/255, 308, 310, 464, 465, 466, 484
See application file for complete search history.

(56) References Cited

U.S. PATENT DOCUMENTS 5,509,902 A    4/1996  Raulerson
5,741,333 A    4/1998  Friday
(Continued)

FOREIGN PATENT DOCUMENTS

EP    0 266 035 A1    8/1987
EP    0 331 764 A1    3/1988
(Continued)

OTHER PUBLICATIONS

Office Action in related Japanese Patent Application No. 2012-157029 (dated Apr. 11, 2014).
(Continued)

*Primary Examiner* — Leo B Tentoni
(74) *Attorney, Agent, or Firm* — Brinks Gilson & Lione

(57) ABSTRACT

A method for making a graft layer is provided. The graft layer has at least two layers with different porosities. The two layers are applied by electrospinning. The parameters of the electrospinning may be varied when applying the first and second layers in order to achieve different porosities of the first and second layers.

20 Claims, 1 Drawing Sheet

Related U.S. Application Data

(60) Provisional application No. 61/508,421, filed on Jul. 15, 2011.

(51) Int. Cl.

| | | |
|---|---|---|
| *A61L 31/04* | (2006.01) | |
| *D01D 5/00* | (2006.01) | |
| *D04H 1/728* | (2012.01) | |
| *D04H 3/073* | (2012.01) | |
| *B29C 47/00* | (2006.01) | |
| *B29C 47/06* | (2006.01) | |
| *A61F 2/07* | (2013.01) | |
| *B29K 75/00* | (2006.01) | |
| *B29K 83/00* | (2006.01) | |
| *B29L 9/00* | (2006.01) | |
| *B29L 23/20* | (2006.01) | |
| *B29L 31/00* | (2006.01) | |

(52) U.S. Cl.
CPC .............. *A61F 2/07* (2013.01); *B29K 2075/00* (2013.01); *B29K 2083/00* (2013.01); *B29L 2009/00* (2013.01); *B29L 2023/20* (2013.01); *B29L 2031/7546* (2013.01); *B32B 2250/03* (2013.01)

(56) References Cited

U.S. PATENT DOCUMENTS

| | | |
|---|---|---|
| 6,498,207 B1 | 12/2002 | Hoshikawa et al. |
| 2002/0198588 A1 | 12/2002 | Armstrong et al. |
| 2003/0040772 A1 | 2/2003 | Hyodoh et al. |
| 2003/0114917 A1 | 6/2003 | Holloway et al. |
| 2004/0016260 A1 | 1/2004 | Kobayashi et al. |
| 2005/0137675 A1 | 6/2005 | Dubson et al. |
| 2007/0237973 A1 | 10/2007 | Purdy et al. |
| 2008/0119943 A1 | 5/2008 | Armstrong et al. |
| 2008/0154357 A1 | 6/2008 | Shalev |
| 2009/0012607 A1 | 1/2009 | Kim et al. |
| 2009/0074832 A1 | 3/2009 | Zussman et al. |
| 2009/0163994 A1 | 6/2009 | Quigley et al. |
| 2010/0028674 A1 | 2/2010 | Ochanda |
| 2010/0193999 A1 | 8/2010 | Anneaux et al. |
| 2010/0233115 A1 | 9/2010 | Patel et al. |
| 2011/0135806 A1 | 6/2011 | Grewe et al. |
| 2011/0155956 A1 | 6/2011 | Ashraf et al. |

FOREIGN PATENT DOCUMENTS

| | | |
|---|---|---|
| GB | 2 195 251 A | 4/1988 |
| JP | 63-119756 | 5/1988 |
| JP | 11-504548 | 4/1999 |
| JP | 2002-510985 | 4/2002 |
| JP | 2004-532665 | 10/2004 |
| JP | 2005-511242 | 4/2005 |
| JP | 2010-528812 | 8/2010 |
| WO | WO 97/25938 | 7/1997 |
| WO | WO 98/26731 | 6/1998 |
| WO | WO 02/49535 A2 | 6/2002 |
| WO | WO 02/49536 A2 | 6/2002 |
| WO | WO 02/49536 A3 | 6/2002 |
| WO | WO 03/051233 A1 | 6/2003 |
| WO | WO 2008/106176 A1 | 9/2008 |
| WO | WO 2008/156683 A1 | 12/2008 |
| WO | WO 2011/056705 A2 | 5/2011 |
| WO | WO 2012/103501 A1 | 8/2012 |

OTHER PUBLICATIONS

International Search Report for related application No. 2012205125 dated May 23, 2013.
Patent and Search Report for related Australian Patent Application No. 2012205125 dated Feb. 11, 2013.
Communication pursuant to Article 94(3) EPC for related EPO Application No. 12 176 446.8-1377 4 pgs.

METHOD FOR ELECTROSPINNING A GRAFT LAYER

This is a Continuation of application Ser. No. 13/548,956 filed on Jul. 13, 2012, now U.S. Pat. No. 9,163,333, which claims priority from Provisional Application No. 61/508,421 filed Jul. 15, 2011, both of which are incorporated by reference herein in their entireties.

BACKGROUND

The present invention relates generally to medical devices and more particularly to a graft layer.

Stents have become relatively common devices for treating a number of organs, such as the vascular system, colon, biliary tract, urinary tract, esophagus, trachea and the like. Stents are useful in treating various ailments including blockages, occlusions, narrowing conditions and other related problems that restrict flow through a passageway (generally referred to as a stenosis). Stents are also useful in a variety of other medical procedures including treating various types of aneurysms.

For example, stents may be used to treat numerous vessels in the vascular system, including coronary arteries, peripheral arteries (e.g., carotid, brachial, renal, iliac and femoral), and other vessels. Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that is risky and requires a long recovery time for the patient. By contrast, stenting procedures are performed transluminally and do not require open surgery. Thus, recovery time is reduced and the risks of surgery are minimized.

Many different types of stents and stenting procedures are possible. In general, however, stents are typically designed as tubular support structures that may be inserted percutaneously and transluminally through a body passageway. Typically, stents are made from a structure that wraps around at least a portion of a circumference and are adapted to compress and expand between a smaller and larger diameter. Stents may be self-expanding so that they elastically expand out to the larger diameter, or may be balloon-expandable so that they require a force to expand to the larger diameter. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway. Conversely, stents may also be used to support a graft layer to prevent fluid flow through the side walls of the stent. However, these are only some of the examples of how stents may be used, and stents may be used for other purposes as well.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

SUMMARY

A method for electrospinning a graft layer is described. The graft layer may have two layers that are electrospun using different electrospinning parameters so that the inner layer is more porous than the outer layer. For example, a larger needle may be used and the flow rate increased when the electrospinning the outer layer. Alternatively, other parameters may be varied when electrospinning the inner and outer layers. The inventions herein may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
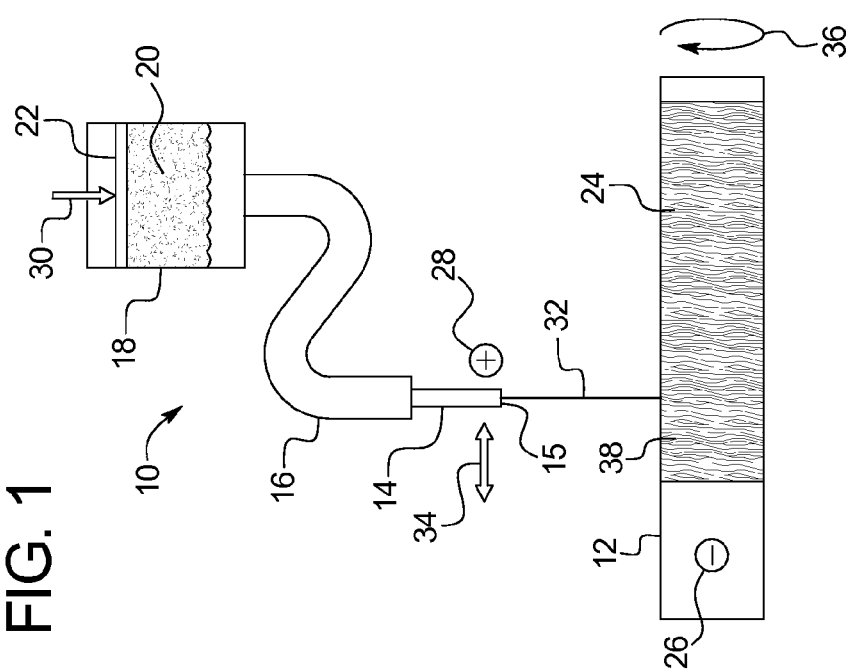
FIG. 1 is a schematic view of an electrospinning apparatus applying a first graft layer onto a mandrel.

Referring now to the figures, and particularly to FIG. 1, an electrospinning apparatus 10 is shown for making a graft 24. The electrospinning apparatus 10 includes a mandrel 12 that is rotatable relative to a needle 14. However, it is also possible for the mandrel 12 to be non-rotatable and the needle 14 to rotate around the mandrel 12 if desired. The needle 14 is positioned a distance away from the mandrel 12 and translates relative to the mandrel 12. However, it is also possible for the needle 14 to not translate and the mandrel 12 to translate if desired. A tube 16 may be fluidly connected to the needle 14 and to a reservoir 18. The reservoir 18 may contain a mixture 20 of polymer and solvent so that the mixture 20 is viscous and flowable through the tube 16 and the needle 14. A piston 22 may be provided in the reservoir 18 to apply pressure to the polymer/solvent mixture 22 to control the flow rate through the needle 14.

In order to form a graft layer 24 with the electrospinning apparatus 10, the mandrel 12 and needle 14 are charged 26, 28 oppositely of each other. For example, the mandrel 12 may be negatively charged 26 and the needle 14 may be positively charged 28. However, the charges 26, 28 of the mandrel 12 and the needle 14 may be reversed if desired. Pressure 30 is then applied to the polymer/solvent mixture 20 in the reservoir 18 by the piston 22 to force the polymer/solvent mixture 20 through the tube 16 to the needle 14. The polymer/solvent mixture 20 continues to flow from the tube 16 through a lumen in the needle 14 to a dispensing opening 15 at the end of the needle 14. At the dispensing opening 15, the polymer/solvent mixture 20 exits the needle 14, and one or more fibers 32 of the polymer/solvent mixture 20 spray or shoot toward the mandrel 12. As the polymer/solvent mixture 20 passes through the needle 14, the polymer/solvent mixture 20 also becomes charged by the charge 28 of the needle 14. Since this charge is opposite of the charge 26 of the mandrel 12, the charged polymer/solvent mixture 20, 32 is attracted to the mandrel 12. As the polymer/solvent mixture 20, 32 is dispensed from the needle 14 toward the mandrel 12, the needle 14 and mandrel 12 are translated 34 and rotated 36 relative to each other. As a result, a layer 38 of polymer/solvent fibers 32 is applied to the mandrel 12. The solvent eventually dissipates from the polymer/solvent mixture 20 so that the resulting fiber layer 38 is composed substantially of the polymer.

Figure 2:
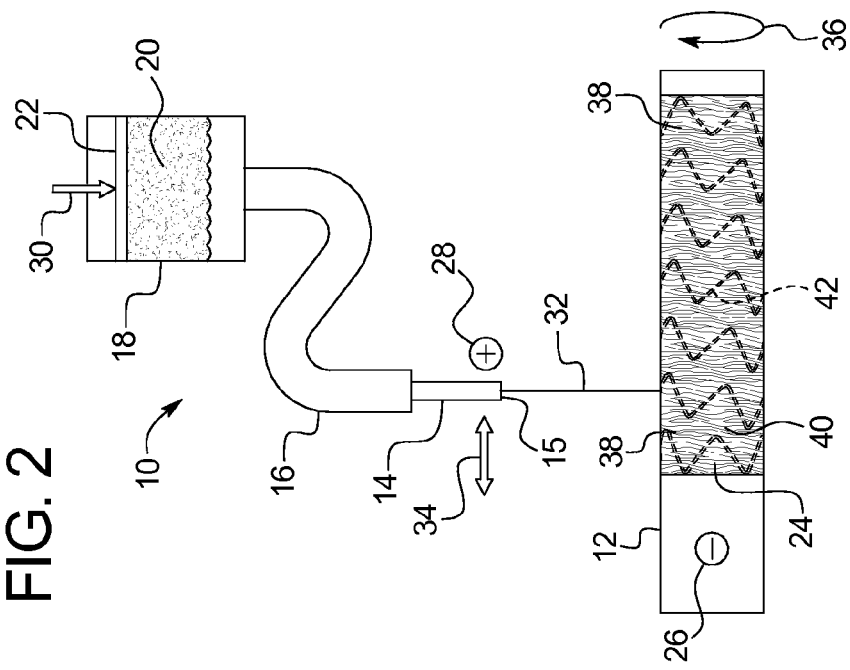
FIG. 2 is a schematic view of the electrospinning apparatus applying a second graft layer onto a stent and the first layer.

After the first fiber layer 38 has been electrospun onto the mandrel 12, a second fiber layer 40 may be electrospun onto the first fiber layer 38 to form a graft 24 with at least two different electrospun layers 38, 40. Preferably, the two fiber layers 38, 40 solvent bond to each other to adhere the two layers 38, 40 together. As shown in FIG. 2, if desired, a stent 42 may be positioned between the two layers 38, 40, with the two layers 38, 40 being adhered to each other through open spaces in the stent 42 wall. The two fiber layers 38, 40 may be electrospun using different parameters so that the porosity of the two fiber layers 38, 40 are different from each other. For example, the inner fiber layer 38 may be more porous than the outer fiber layer 40. This may be useful to encourage endothelization on the more porous inner layer 38 of the graft 24, and yet, increase structural stability of the graft 24 by providing a less porous outer layer 40 that is more resistant to stresses and provides more surface area for adherence to the inner layer 38. The less porous outer layer 40 may also be useful in preventing endoleaks. The different porosities for the inner and outer layers 38, 40 may be achieved by using a second needle 14' for the outer layer 40 that has a larger lumen than a first needle 14 used for the inner layer 38. In addition, the flow rate of the polymer/solvent mixture 20 may be higher through the second needle 14' when forming the outer layer 40 than the flow rate through the first needle 14 when forming the inner layer 38. Alternatively, other parameters may be varied when electrospinning two different layers 38, 40 to achieve different porosities. For example, the polymer and/or solvent 20; temperature; humidity; distance between the needle 14, 14' dispensing opening 15 and the mandrel 12; and the rotational 36 and/or translational 34 speed of the mandrel 12 and needle 14, 14' may be varied.

Preferably, the polymer/solvent mixture 20 for the first and second layers 38, 40 is thoralon mixed with dimethylacetamide as a solvent. The thoralon/dimethylacetamide mixture may be about 10% to about 23.5% thoralon by weight. More preferably, the thoralon/dimethylacetamide mixture may be about 10% to about 15% thoralon by weight. Most preferably, the thoralon/dimethylacetamide mixture may be about 12.5% thoralon by weight. Preferably, the lumen of the first needle 14 for the first layer 38 may be about 0.011" to about 0.014" in diameter or about a 27 gauge needle to about a 23 gauge needle. Preferably, the lumen of the second needle 14' for the second layer 40 may be about 0.017" to about 0.0345" in diameter or about a 22 gauge needle to about a 18 gauge needle. Thus, the second needle 14' is at least one gauge larger than the first needle 14 with a lumen that is at least about 0.003" larger than the lumen of the first needle 14. Most preferably, the lumen of the first needle 14 for the first layer 38 may be about 0.014" (23 gauge) and the lumen of the second needle 14' for the second layer 40 may be about 0.017" (22 gauge). The flow rate for the first layer 38 may be about 0.4 mL/hr to about 0.5 mL/hr, and the flow rate for the second layer 40 may be about 0.6 mL/hr to about 0.9 mL/hr. The total volume of the polymer/solvent mixture 20 used to make the first and second layers 38, 40 may be controlled by dispensing about 0.35 mL to about 0.5 mL per 150 mm length of the first layer 38 and dispensing about 1.1 mL to about 1.3 mL per 150 mm length of the second layer 40.

The temperature and humidity may be constant when electrospinning the first and second layers 38, 40. For example, the temperature may be about 26° C. to about 29° C., and the humidity may be about 35% to about 40%. Alternatively, the temperature and humidity may be varied when electrospinning the first and second layers 38, 40. For example, the humidity may be higher when electrospinning the first layer 38 than when electrospinning the second layer 40. When the solvent is hygroscopic, such as dimethylacetamide, this causes more of the solvent to be drawn away from the polymer/solvent fibers 20, 32 as the fibers 32 pass between the dispensing opening 15 of the needle 14' and the mandrel 12. This occurs because hygroscopic solvents have an affinity for moisture. Thus, some of the solvent dissipates from the polymer/solvent mixture 20, 32 between the needle 14' and the mandrel 12. This allows the polymer/solvent mixture 20 to maintain a desirable viscosity to flow through the tube 16 and the needle 14', and yet, be relatively dry (that is, having less solvent) when the fiber 32 contacts the mandrel 12. For example, the humidity may be about 55% to about 65% when electrospinning the first layer 38. By contrast, the humidity may be about 35% to about 42% when electrospinning the second layer 40. Most preferably, the humidity may be about 38.5% when electrospinning the second layer 40. As a result, the fibers 32 in the second layer 40 are applied to the mandrel 12 and/or stent 42 in a more wet state with more solvent remaining in the mixture. This may be useful to permit the fibers 32 in the outer layer 40 to flow more after contacting the mandrel 12 and/or stent 42 so that the outer layer 40 fibers 32 form a less porous structure and more completely bond to the inner layer 38.

The distal openings 15 of the first and second needles 14, 14' may be positioned about 15 cm to about 25 cm from the mandrel 12. More preferably, the distal openings 15 of the first and second needles 14, 14' may be positioned about 20 cm from the mandrel 12. When the apparatus 10 is electrospinning the first and second layers 38, 40, the first and second needles 14, 14' may translate at a rate of about 0.1 mm/s to about 0.9 mm/s, and most preferably 0.5 mm/s, and the mandrel 12 may rotate about 500 rpm to about 750 rpm. The first and second needles 14, 14' may be positively charged about 10 kV to about 15 kV, and the mandrel may be negatively charged about 10 kV to about 20 kV. More preferably, the first and second needles 14, 14' may be positively charged to about 10 kV and the mandrel may be negatively charged to about 14 kV. When electrospinning the second layer 40 onto the stent 42, it may not be necessary to separately charge the stent 42 to attract the electrospun fibers 32, since the first layer 38 may not insulate the stent 42 from the mandrel 12 sufficiently to significantly reduce the attraction of the fibers 32. In order to remove the graft layer 24 from the mandrel 12 after the first and second layers 38, 40 have been electrospun, it may be preferable that the mandrel 12 be highly polished so that the graft layer 24 may be slid off mandrel 12 without tearing the graft layer 24.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method of making a stent-graft with an inner layer and an outer layer where the outer layer is less porous than the inner layer, comprising:
   applying a first charge to a mandrel;
   applying a second charge to a first needle;
   rotating and translating said mandrel and said first needle relative to each other;
   dispensing a first polymer mixed with a first solvent through said first needle at a first flow rate, a first layer of fibers thereby being electrospun onto said mandrel;
   disposing a stent onto said first layer; thereafter
   applying a third charge to said mandrel;
   applying a fourth charge to a second needle;
   rotating and translating said mandrel and said second needle relative to each other; and
   dispensing a second polymer mixed with a second solvent through said second needle at a second flow rate, a second layer of fibers thereby being electrospun onto said stent;
   wherein said second needle has a larger lumen than said first needle and said second flow rate is higher than said first flow rate.

2. The method according to claim 1, wherein said first polymer mixed with said first solvent and said second polymer mixed with said second solvent comprises a polyetherurethane urea blended with a siloxane containing surface modifying additive mixed with dimethylacetamide.

3. The method according to claim 2, wherein said first polymer mixed with said first solvent and said second polymer mixed with said second solvent comprises about 10% to about 23.5% by weight of the polyetherurethane urea blended with a siloxane containing surface modifying additive.

4. The method according to claim 1, wherein said first needle has a lumen about 0.011" to about 0.014" in diameter and said second needle has a lumen about 0.017" to about 0.0345" in diameter.

5. The method according to claim 1, wherein said first flow rate is about 0.4 mL/hr to about 0.5 mL/hr and said second flow rate is about 0.6 mL/hr to about 0.9 mL/hr.

6. The method according to claim 5, wherein about 0.35 mL to about 0.5 mL of said first polymer mixed with said first solvent is dispensed from said first needle for electrospinning said first layer of fibers onto said mandrel per 150 mm of said first layer, and about 1.1 mL to about 1.3 mL of said second polymer mixed with said second solvent is dispensed from said second needle for electrospinning said second layer of fibers onto said stent per 150 mm of said second layer.

7. The method according to claim 1, wherein a temperature and humidity during said dispensing of said first polymer mixed with said first solvent and during said dispensing of said second polymer mixed with said second solvent is about 26° C. to about 29° C. and about 35% to about 42%, respectively.

8. The method according to claim 1, wherein said first and second solvents are hygroscopic, a first humidity during said dispensing of said first polymer mixed with said first solvent is about 55% to about 65%, and a second humidity during said dispensing of said second polymer mixed with said second solvent is about 35% to about 42%.

9. The method according to claim 1, wherein a distance between dispensing openings of said first and second needles and said mandrel during said dispensing of said first polymer mixed with said first solvent and during said dispensing of said second polymer mixed with said second solvent is about 15 cm to about 25 cm.

10. The method according to claim 1, wherein said first and second needles translate about 0.1 mm/s to about 0.9 mm/s and said mandrel rotates about 500 rpm to about 750 rpm during said dispensing of said first polymer mixed with said first solvent and during said dispensing of said second polymer mixed with said second solvent.

11. The method according to claim 1, wherein said first and second needles are positively charged to about 10 kV to about 15 kV and said mandrel is negatively charged to about 10 kV to about 20 kV during said dispensing of said first polymer mixed with said first solvent and during said dispensing of said second polymer mixed with said second solvent.

12. The method according to claim 1, wherein said first layer is defined by a first porosity that effectively encourages endothelization and said second layer is defined by a second porosity that effectively prevents endoleaks.

13. The method according to claim 12, wherein said first polymer mixed with said first solvent and said second polymer mixed with said second solvent comprises about 10% to about 23.5% by weight of a polyetherurethane urea blended with a siloxane containing surface modifying additive, and said first needle has a lumen about 0.011" to about 0.014" in diameter and said second needle has a lumen about 0.017" to about 0.0345" in diameter.

14. The method according to claim 13, wherein said first flow rate is about 0.4 mL/hr to about 0.5 mL/hr and said second flow rate is about 0.6 mL/hr to about 0.9 mL/hr.

15. The method according to claim 14, wherein a temperature and humidity during said dispensing of said first polymer mixed with said first solvent and during said dispensing of said second polymer mixed with said second solvent is about 26° C. to about 29° C. and about 35% to about 42%, respectively.

16. The method according to claim 14, wherein a first humidity during said dispensing of said first polymer mixed with said first solvent is about 55% to about 65% and a second humidity during said dispensing of said second polymer mixed with said second solvent is about 35% to about 42%.

17. The method according to claim 14, wherein about 0.35 mL to about 0.5 mL of said first polymer mixed with said first solvent is dispensed from said first needle for electrospinning said first layer of fibers onto said mandrel per 150 mm of said first layer, and about 1.1 mL to about 1.3 mL of said second polymer mixed with said second solvent is dispensed from said second needle for electrospinning said second layer of fibers onto said stent per 150 mm of said second layer.

18. The method according to claim 17, wherein a temperature and humidity during said dispensing of said second polymer mixed with said second solvent is about 26° C. to about 29° C. and about 35% to about 42%, respectively, and a distance between dispensing openings of said first and second needles and said mandrel during said dispensing of said first polymer mixed with said first solvent and during said dispensing of said second polymer mixed with said second solvent is about 15 cm to about 25 cm.

19. The method according to claim 18, wherein said first and second needles translate about 0.1 mm/s to about 0.9 mm/s and said mandrel rotates about 500 rpm to about 750 rpm during said dispensing of said first polymer mixed with said first solvent and during said dispensing of said second polymer mixed with said second solvent, said first and second needles are positively charged to about 10 kV to about 15 kV and said mandrel is negatively charged to about 10 kV to about 20 kV during said dispensing of said first polymer mixed with said first solvent and during said dispensing of said second polymer mixed with said second solvent, and a temperature and humidity during said dispensing of said first polymer mixed with said first solvent is about 26° C. to about 29° C. and about 55% to about 65%, respectively.

20. A method of making a stent-graft with an inner layer and an outer layer
where the outer layer is less porous than the inner layer, comprising:
applying a first charge to a mandrel;
applying a second charge to a first needle;
rotating and translating said mandrel and said first needle relative to each other;
dispensing a first polymer mixed with a first solvent through said first needle at
a first flow rate, a first layer of fibers thereby being electrospun onto said mandrel;
disposing a stent onto said first layer; thereafter
applying a third charge to said mandrel;
applying a fourth charge to a second needle;
rotating and translating said mandrel and said second needle relative to each other; and
dispensing a second polymer mixed with a second solvent through said second needle at a second flow rate, a second layer of fibers thereby being electrospun onto said stent;
wherein said second needle has a larger lumen than said first needle and said second flow rate is higher than said first flow rate;
wherein said first and second solvents are hygroscopic.

* * * * *